US010160993B2

(12) United States Patent
Parker et al.

(10) Patent No.: US 10,160,993 B2
(45) Date of Patent: Dec. 25, 2018

(54) TYROSINE KINASE BIOSENSORS AND METHODS OF USE

(71) Applicant: Purdue Research Foundation, West Lafayette, IN (US)

(72) Inventors: Laurie L. Parker, Minneapolis, MN (US); Wei Cui, Chengdu (CN)

(73) Assignee: Purdue Research Foundation, West Lafayette, IN (US)

( * ) Notice: Subject to any disclaimer, the term of this patent is extended or adjusted under 35 U.S.C. 154(b) by 39 days.

(21) Appl. No.: 15/127,788

(22) PCT Filed: Mar. 20, 2015

(86) PCT No.: PCT/US2015/021657
§ 371 (c)(1),
(2) Date: Sep. 20, 2016

(87) PCT Pub. No.: WO2015/143264
PCT Pub. Date: Sep. 24, 2015

(65) Prior Publication Data
US 2017/0183710 A1 Jun. 29, 2017

Related U.S. Application Data

(60) Provisional application No. 61/968,876, filed on Mar. 21, 2014.

(51) Int. Cl.
*C12Q 1/48* (2006.01)
*C07K 7/08* (2006.01)
*C07K 14/705* (2006.01)
*C12N 9/12* (2006.01)

(52) U.S. Cl.
CPC .............. *C12Q 1/485* (2013.01); *C07K 7/08* (2013.01); *C07K 14/705* (2013.01); *C12N 9/1205* (2013.01); *C12Q 1/48* (2013.01); *C12Y 207/10001* (2013.01); *G01N 2440/14* (2013.01); *G01N 2500/02* (2013.01); *G01N 2500/20* (2013.01)

(58) Field of Classification Search
CPC .................................. C12Q 1/48; C07K 7/08
See application file for complete search history.

(56) References Cited

U.S. PATENT DOCUMENTS

| | | | | |
|---|---|---|---|---|
| 5,607,859 A | * | 3/1997 | Biemann | H01J 49/145 436/173 |
| 5,646,120 A | * | 7/1997 | Sumner-Smith | A61K 38/08 514/3.7 |
| 5,770,421 A | * | 6/1998 | Morris | C07K 14/47 435/194 |
| 6,174,674 B1 | * | 1/2001 | Morris | C07K 14/47 435/6.11 |
| 2001/0021505 A1 | * | 9/2001 | Morris | C07K 14/47 435/6.11 |
| 2003/0013848 A1 | | 1/2003 | Lemke et al. | |
| 2003/0105057 A1 | | 6/2003 | Fu et al. | |
| 2004/0171075 A1 | | 9/2004 | Flynn et al. | |
| 2012/0101108 A1 | | 4/2012 | Haack et al. | |
| 2013/0231265 A1 | | 9/2013 | Parker et al. | |

OTHER PUBLICATIONS

UniProtKB Entry B3RT14_TRIAD, Sep. 2, 2008 (online) <URL: https://www.uniprot.org/uniprot/B3RT14>.
International Search Report for PCT/US2015/021657, dated Jul. 28, 2015, (online)<URL: https://patentscope.wipo.int/search/docservicepdf_pct/id00000031488071/ISR/WO2015143264.pdf>.
Written Opinion of the International Searching Authority for PCT/US2015/021657, dated Jun. 30, 2015, <https://patentscope.wipo.int/search/docservicepdf_pct/id00000031491141/WOSA/WO2015143264.pdf>.

\* cited by examiner

*Primary Examiner* — Amber D Steele
(74) *Attorney, Agent, or Firm* — D'Hue Law LLC; Cedric A. D'Hue (57) ABSTRACT

The present disclosure illustrates new synthetic ALK-specific biosensors used to measure the activity or ALK, and methods of using the synthetic ALK-specific biosensors in assays, including high throughput assays.

10 Claims, 6 Drawing Sheets

Specification includes a Sequence Listing.

TYROSINE KINASE BIOSENSORS AND METHODS OF USE

CROSS-REFERENCE TO RELATED APPLICATIONS

The present U.S. patent application is related to and claims the priority benefit of U.S. Provisional Patent Application Ser. No. 61/968,876, filed Mar. 21, 2014, the contents of which is hereby incorporated by reference in its entirety into this disclosure.

STATEMENT GOVERNMENT INTEREST

This invention was made with government support under CA160129 awarded by the National Institutes of Health. The government has certain rights in the invention.

TECHNICAL FIELD

This present disclosure generally relates to a synthetic sequence to generate a ligand to bind to a specific tyrosine kinase and methods to manufacture, and in particular to a synthetic peptide that binds terbium when phosphorylated by a specific kinase of interest, and method to design such a peptide.

BACKGROUND

This section introduces aspects that may help facilitate a better understanding of the disclosure. Accordingly, these statements are to be read in this light and are not to be understood as admissions about what is or is not prior art.

Anaplastic lymphoma kinase (ALK) is a receptor tyrosine kinase, believed to play an important role in the development and function of the nervous system. ALK is normally expressed in the central nervous system, with peak expression during the neonatal period. However, due to chromosomal translocations, ALK is also aberrantly expressed and activated in some cancers in the form of oncogenic fusion proteins. ALK fusion proteins are responsible for approximately 5-10% of all non-Hodgkin's lymphomas. The annual incidence of ALK positive lymphomas is about 100,000 worldwide, with 2000-3000 new cases occurring in EU countries. ALK is an excellent candidate for therapeutic intervention, as it plays an essential role in oncogenicity and its normal expression is mostly restricted to the central nervous system. Hence, understanding ALK's role in cancer genesis and response to various drug and drug-candidates would be of great benefit to society.

There is a need in the art for compositions and methods of measuring activity of tyrosine kinases, including ALK kinase. The compositions and methods described herein address that need.

SUMMARY

The present invention relates generally to compositions and methods for assaying tyrosine kinase activity, and specifically to measuring the activity of ALK.

In certain embodiments, the invention includes a biosensor comprising a peptide comprising a substrate sequence, i.e., an amino acid sequence including a tyrosine residue that can be phosphorylated by a tyrosine kinase. In certain embodiments, the biosensor includes a substrate sequence that can be phosphorylated by ALK. In certain embodiments, the biosensor includes one or more additional functional elements. In some embodiments, the functional elements include an affinity tag to facilitate capture, isolation or immobilization of the biosensor, a cleavable linker, or a cell penetrating peptide. In certain embodiments, the biosensor may include an affinity tag, such as biotin or a poly-His tag. In certain embodiments, the biosensor may include a cell penetrating peptide. In certain embodiments, the cell penetrating peptide may be Tat. In certain embodiments, the biosensor may include a cleavable linker, such as a photocleavable linker. The photocleavable linker may include, for example, a photocleavable amino acid analog such as beta (nitrophenyl)alanine. The photocleavable linker covalently links two other elements of the biosensor. For example, the substrate sequence may be linked to an affinity tagged peptide sequence which is in turn linked through a photocleavable linker to a cell penetrating peptide. In other embodiments, the biosensor is designed to include a photocleavable linker between the substrate sequence and affinity tag.

In certain embodiments, the biosensor comprises a substrate sequence for ALK. In certain embodiments an ALK-specific biosensor comprises a peptide comprising a substrate sequence, the substrate sequence comprising a core sequence $FX_2MX_4RDX_7YX_9X_{10}X_{11}FFRRKGG$ (SEQ ID NO:11), wherein $X_2$ is a polar uncharged amino acid or polar acidic amino acid; $X_4$ is a nonpolar hydrophobic amino acid, polar uncharged amino acid, or polar acidic amino acid; $X_7$ is a nonpolar hydrophobic amino acid or polar basic amino acid; $X_9$ is a polar basic amino acid or polar uncharged amino acid; $X_{10}$ is a nonpolar hydrophobic amino acid, a polar acidic amino acid, or a polar uncharged amino acid; and $X_{11}$ is a polar uncharged amino acid.

In certain embodiments, the biosensor comprises a substrate sequence for ALK. In certain embodiments an ALK-specific biosensor comprises a peptide comprising a substrate sequence, the substrate sequence comprising a core amino acid sequence $FX_2MX_4RDX_7YX_9X_{10}X_{11}FFRRKGG$ (SEQ ID NO:12), wherein $X_2$ is G or D; $X_4$ is A or D; $X_7$ is I or H; $X_9$ is R or T; $X_{10}$ is M, D, or N; and $X_{11}$ is S, or T;

In certain embodiments, the composition may include an ALK-specific biosensor comprising a synthetic substrate sequence selected from the group consisting of FDMDRDI-YRMSFFRKGGK$_b$GG (SEQ ID NO:1), FDMDRDI-YTNTFFRKGGK$_b$GG (SEQ ID NO:2), FDMDRDI-YRMSFFRKGGKGG (SEQ ID NO:3), FDMDRDIYTNTFFRKGGKGG (SEQ ID NO:4), FDMDRDIYRDSFFRKGGK$_b$GG (SEQ ID NO:5), FDMDRDI-YRDSFFRKGGKGG (SEQ ID NO:6), FDMDRDIYRNTF-FRKGGK$_b$GG (SEQ ID NO:7), and FDMDRDIYRNTFFRKGGKGG (SEQ ID NO:8). The symbol "$K_b$" represents biotinylated lysine.

In other embodiments are provided methods for detecting tyrosine kinase activity. In certain embodiments, the methods allow detection of the activity of ALK by detecting phosphorylation of a substrate sequence of ALK. In certain embodiments, the methods allow "multiplexing" of the detection of tyrosine kinase activity, i.e., detecting the activity of two or more tyrosine kinases in a single reaction when combining an ALK-specific biosensor with other kinase-specific biosensors in a single assay. In certain embodiments, the assay is conducted in vitro, including cell lysates or whole cells. In certain embodiments, phosphorylation is detected using ELISA, terbium based time-resolved luminescence, MALDI-TOF MS analysis, or multiple reaction monitoring (MRM) on a triple quadrupole mass spectrometer. In certain embodiments, the method is conducted using a substrate sequence or a biosensor comprising the substrate that covalently attached directly or indirectly through an affinity tag to a solid surface, such as a bead, a multi-well plate, or nanoparticle.

In certain embodiments, the methods of the invention may be used to determine the level of tyrosine kinase activity in a biological sample from a mammal, such as a human. In certain embodiments, the methods involve detecting ALK activity in a sample from a person suspected of having or at risk for developing a condition associated with altered tyrosine kinase activity, i.e., tyrosine kinase activity that is increased or decreased relative to the tyrosine kinase activity of a control, e.g., a sample from a person who does not have the condition, or a normal range of tyrosine kinase activity based on the tyrosine kinase activities of samples from a relevant sample of people. In certain embodiments, the sample includes lymphocytic cells, or cancer cells of epithelial origin. In certain embodiments, the results of the determination may be used in diagnosis or prognosis, or in determining a course of treatment.

In certain embodiments, the methods involve determining the level of ALK activity in a person. In certain embodiments, the person has an oncogene where the alk gene has undergone a genetic mutation resulting in a translocation, genetic modification (i.e. mutation), or is upregulated by additional active copies of the gene in a single cell or upregulation by some other molecular mechanism. In certain embodiments, the method may involve recommending treatment or treating a person with mutated ALK having an increased level of ALK activity relative to a control with an ALK inhibitor. In certain embodiments, the method involves determining the level of ALK activity in a person. In certain embodiments in which the person has a disorder associated with increased ALK activity, treatment may include administering to the person an effective amount of an ALK inhibitor, such as an siRNA or small molecule ALK inhibitor, some of which are known in the art. In certain embodiments, the method may involve recommending treatment or treating a person with a disorder associated with an ALK fusion kinase, due to a translocation event. In certain embodiments in which the person has a disorder associated with a mutated alk gene, treatment may include administering to the person an effective amount of an ALK inhibitor, such as an siRNA or small molecule ALK inhibitor, some of which are known in the art.

In certain embodiments, the methods involve determining the level of ALK activity in a sample from a person with lung cancer. In certain embodiments, the method involves recommending treatment or treating a person with lung cancer, the treatment including administering an effective amount of a treatment.

In certain embodiments, the methods can be used to determine whether a person with a cancer is likely to benefit from a particular treatment. For example, in certain embodiments, the methods of the invention can be used to detect tyrosine kinase activity in whole cells obtained from the person in the presence and absence of an inhibitor of the tyrosine kinase. In certain embodiments, the methods employ an ALK biosensor to measure phosphorylation in whole cells from a person with cancer associated with aberrant ALK activity to assess whether the cells are sensitive or resistant to treatment such as crizotinib. In certain embodiments, phosphorylation levels of cells treated or not treated with crizotinib in vitro are compared, with the absence of a sufficient decrease in phosphorylation of the substrate sequence from crizotinib treated cells suggesting that the cancer may not respond to treatment with the inhibitor. In other embodiments, samples are taken from the person with cancer at different times to monitor effectiveness as measured by a sustained decrease in phosphorylation of the ALK biosensor following treatment with a small molecule such as crizotinib. In certain embodiments, the methods are performed using MRM on a triple quadrupole mass spectrometer using relatively few cells, e.g., from 10,000 to 50,000 cells, making testing of clinical samples feasible.

In other embodiments, the methods of the invention can be used to screen for molecules capable of altering tyrosine kinase activity, including molecules that reduce or increase tyrosine kinase activity. In certain embodiments are provided methods for screening for inhibitors of ALK. In certain embodiments, the assays are conducted in a high throughput format. In certain embodiments, the methods employ whole cells that are contacted with the biosensor in the presence and absence of the test molecule to assess whether the agent inhibits intracellular phosphorylation of the substrate sequence.

In certain embodiments are provided kits comprising ALK-specific peptide substrates, for example, peptide substrates immobilized on a solid surface, or comprised within a biosensor. In certain embodiments, the kits may be used to perform the methods of the invention. In certain embodiments, the kits may contain additional components, including, for example, suitable buffers, ALK, and a phosphorylation detection reagent such as antibodies or terbium.

In certain embodiments a method of detecting phosphorylation of an ALK-specific biosensor comprising: contacting the ALK-specific biosensor with an ALK and terbium; exposing the ALK-specific biosensor to light of a wavelength of about 250 to 500 nm; and measuring the emission spectrum of the exposed ALK-specific biosensor using time-resolved luminescence to detect phosphorylation of the ALK-specific biosensor

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

This disclosure describes ALK-specific biosensors, to report the enzymatic activity of Anaplastic Lymphoma Kinase (ALK) in vitro. The ALK-specific biosensors include synthetic substrate sequences with high binding affinity for ALK, and may be phosphorylated by ALK on the biosensors' at least one tyrosine residue. One method of designing the ALK-specific biosensors is described in U.S. patent application Ser. No. 13/761,968, the contents of which are incorporated in its entirety. The ALK-specific biosensors are designed to have increased binding affinity for terbium (III) ($Tb^{3+}$) luminescence when phosphorylated, and less so when unphosphorylated. Therefore, when the phosphorylated ALK-specific biosensors are allowed to bind with $Tb^{3+}$, the degree of ALK-specific biosensor phosphorylation is proportional to the intensity of $Tb^{3+}$ luminescence emission.

The following are exemplary illustrations of the ALK-specific biosensors and their characterization.

ALK-specific biosensors were synthesized having the following synthetic substrate sequences. "Anaplastic Lymphoma kinase Artificial Substrate peptide-A" (ALAStide-A): FDMDRDIYRMSFFRKGGK$_b$GG (SEQ ID NO:1), "Anaplastic Lymphoma kinase Artificial Substrate peptide-B" (ALAStide-B): FDMDRDIYTNTFFRKGGK$_b$GG (SEQ ID NO:2), FDMDRDIYRMSFFRKGGKGG (SEQ ID NO:3), FDMDRDIYTNTFFRKGGKGG (SEQ ID NO:4), FDMDRDIYRDSFFRKGGK$_b$GG (SEQ ID NO:5), FDMDRDIYRDSFFRKGGKGG (SEQ ID NO:6), FDMDRDIYRNTFFRKGGK$_b$GG (SEQ ID NO:7), and FDMDRDIYRNTFFRKGGKGG (SEQ ID NO:8) The symbol "K$_b$" represents biotinylated lysine. The method of synthesis using a peptide synthesizer machine, such as PRELUDE PARALLEL peptide synthesizer, is known in the art.

In accordance with one embodiment, ALK-specific biosensors having a synthetic substrate sequence were designed, synthesized, and screened for the ability to be phosphorylated by ALK. These substrates can be used to identify and quantitate specific kinase activity in vitro. In accordance with one embodiment, the ALK-specific biosensor is introduced into cells and subsequently recovered to indicate the kinase activity in a living cell. In accordance with one embodiment, the ALK-specific biosensor is introduced into the cell using any method, including any of several standard techniques known in the art, including, for example, microinjecting, electroporating, optoporating, vesicle fusing, pinocytic loading, or associating said substrate molecules with membrane permeant peptides. In accordance with one embodiment the ALK-specific biosensor is linked to a cell penetrating peptide. In one embodiment the ALK-specific biosensor is covalently linked to a cell penetrating peptide, optionally through a cleavable linker, to form a biosensor that will be taken up by living cells.

In some embodiments, the ALK-specific biosensor can be linked to a cell penetrating peptide to form a biosensor that can be used to measure specific kinase activity in living cells. In one embodiment the cell penetrating peptide (CPP) is a protein transduction domain or a fragment thereof. Examples of useful CPP include, but are not limited to, the TAT peptide, and the protein transduction domains of Penetratin (pAntp), Transportan, MPG, MPGdeltaNLS, and pHLIP. Cell penetrating fragments of CPP can also be used in a delivery system and/or method of the invention. As used herein, the term CPP includes cell penetrating fragments of protein transduction domains. In accordance with one embodiment the cell penetrating peptide comprises the sequence of RKKRRQRRR (SEQ. NO. 10). In certain embodiments, the CPP can comprise or consist of D-amino acids and/or L-amino acids. For example, a CPP can consist entirely of D-amino acids or entirely of L-amino acids; or a CPP can comprise a mixture of D- and L-amino acids.

In certain embodiments, the amino acid sequence of a CPP can be in the forward direction (i.e. a native peptide) or in the reverse direction. As used herein, reference to a CPP includes both the native and reverse sequences. In one embodiment, the reverse sequence can be a retro-inverso peptide (i.e. the amino acid sequence is the reverse of the native sequence, and consists of D-amino acids). For example, the term "TAT peptide" as used herein includes a retro-inverso TAT peptide comprising a reverse sequence of the protein transduction domain (PTD) of the HIV-1 TAT protein. Examples of other suitable CPP include, without limitation, the PTD of Penetratin (pAntp), Transportan, MPG, MPGdeltaNLS, and pHLIP.

In certain embodiments, the ALK-specific biosensor includes a synthetic substrate sequence linked to one or more tags to facilitate purification of the biosensor and/or to adhere the biosensor to a substrate. In one embodiment the tag is a peptide tag such as His6 (six consecutive histidine residues). In an alternative embodiment the tag is an antigen or biotin. In certain embodiments, the biosensor includes a substrate sequence, a tag, and a CPP.

In certain embodiments, the methods can be used to predict responsiveness of a cancer, which is caused directly or indirectly by an aberrant alk gene, to a therapeutic treatment using relatively few cells. MRM enabled reproducible, selective detection of the peptide biosensor at fmol levels from aliquots of cell lysate equivalent to 15,000 cells. This degree of sensitivity facilitates the miniaturization of the entire assay procedure down to cell numbers approaching 15,000, making it practical for translational applications in patient cells in which the limited amount of available patient material often presents a major challenge.

Prior to assessing ALK activity, a standard curve was prepared using a mixture of phosphorylated and unphosphorylated ALK-specific biosensors, SEQ ID NO:1 and SEQ ID NO:2. To report ALK activity, the ALK-specific biosensors are phosphorylated by ALK in vitro. After allowing the ALK-specific biosensors to become phosphorylated by ALK, the ALK-specific biosensor sample is allowed to bind with $Tb^{3+}$, and $Tb^{3+}$ luminescence is measured in appropriate instruments. The percentage of ALK-specific biosensor phosphorylation can be quantified by intensity of $Tb^{3+}$ luminescence, which represents the enzymatic activity of ALK.

In the following examples showing the characterization of SEQ ID NO:1 and SEQ ID NO:2, the ALK-specific biosensors are compared to a known peptide substrate of ALK in the literature referred to as "YFF peptide" FGMARDIYRASFFRKGGK$_b$GG (SEQ ID NO:9).

Figure 1:
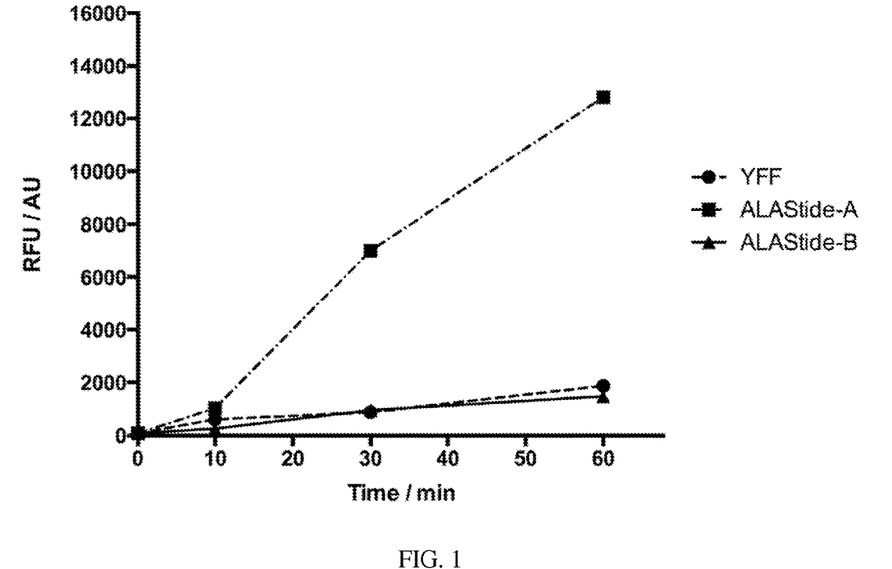
FIG. 1 is a graph illustrating the results of phosphorylation activity of ALAStide-A, ALAStide-B, and YFF peptide when interacting with ALK measured by an ELISA assay.

Referring now to FIG. 1 which illustrates ALAStide-A (SEQ. ID NO. 1) and ALAStide-B (SEQ. ID NO. 2) being phosphorylated by ALK kinase in vitro, the results are obtained by an enzyme-linked immunosorbent assay (ELISA). YFF peptide is used as a reference to compare the phosphorylation activity of ALAStide-A and ALAStide-B. ALAStide-B has comparable phosphorylation level with YFF peptide, and ALAStide-A has higher phosphorylation activity than YFF and ALAStide-B. An example of an experimental condition used in this assay is: 25 µM peptides, 0.1 unit kinase, 100 µM ATP, 10 mM $Mg^{2+}$, 25 mM HEPES buffer (pH=7.5). Total reaction volume is 50 µL, and reaction temperature is set between 35-38° C. At selected time points, 5 µL, sample was taken out and quenched in 20 µL 40 mM EDTA solution. The quenched samples were then used to perform ELISA assay.

Figure 2:
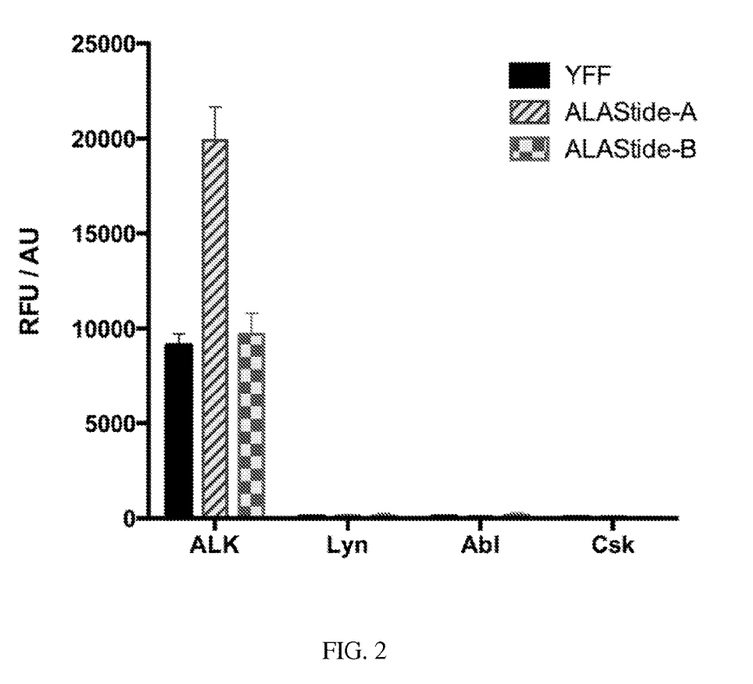
FIG. 2 is a graph illustrating the affinity of ALK to phosphorylate ALAStide-A, ALAStide-B, and YFF peptide and shows the lack of affinity of these the two ALK-specific biosensors and YFF peptide by Lyn, Abl, and Csk.

The specificity of the ALK-specific biosensors, ALAStide-A and ALAStide-B is shown in an ELISA assay, with YFF peptide used as a positive and negative control. The ALK-specific biosensors were assayed for phosphorylation activity against ALK, Lyn, Abl, and Csk. The ALK-specific biosensors are not phosphorylated by other representative cellular kinases, as shown in FIG. 2. YFF peptide, whose kinase specificity (as reported in *Biochemistry* 44, 8533-8542, 2005) is used as a reference. The experimental condition may be similar to those described for the ELISA assay above.

Figure 3A:
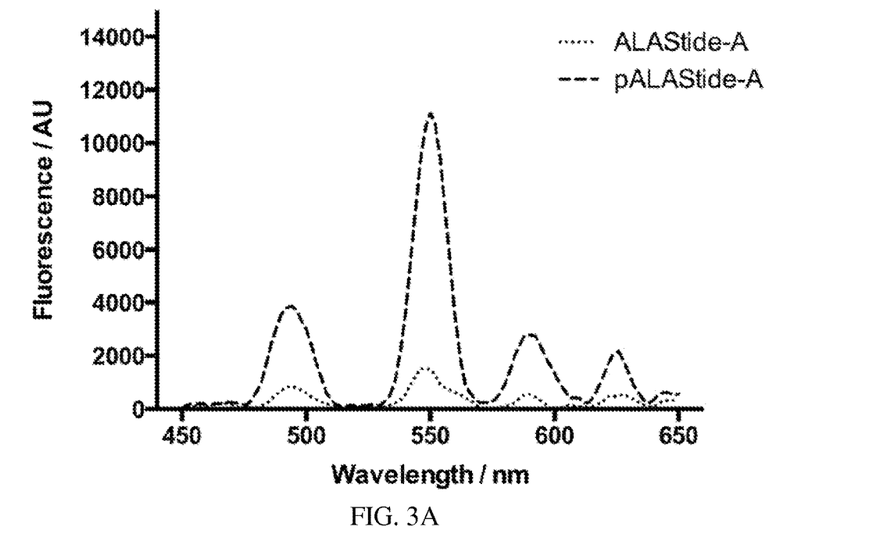
FIG. 3A and FIG. 3B are graphs depicting the difference between levels of terbium luminescence when the ALK-specific biosensors are phosphorylated and not, with the results of ALAStide-A signal when phosphorylated and unphosphorylated in FIG. 3A, and the results of ALAStide-B signal when phosphorylated and unphosphorylated FIG. 3B.
Figure 3B:
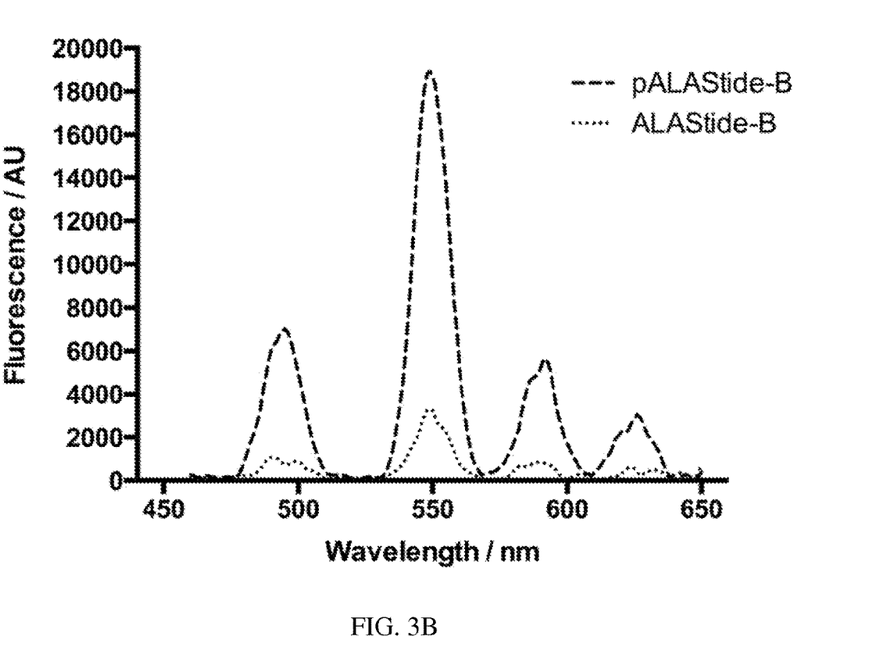

The following is an exemplary illustration of using $TB^{3+}$ luminescence to quantify phosphorylation activity. FIG. 3A and FIG. 3B illustrates the phosphorylated ALK-specific biosensors can sensitize $Tb^{3+}$ luminescence, but the unphosphorylated ALK-specific biosensors cannot. To demonstrate this characteristic, a solution sample contains 20 µM phosphorylated ALAStide-A (pALAStide-A) or phosphorylated ALAStide-B (pALAStide-B), 200 µM $Tb^{3+}$, 100 mM NaCl and 10 mM HEPES buffer (pH=7.5) was prepared. $Tb^{3+}$ luminescence spectrum of this solution was measured in a BIOTEK SYNERGY 4 plate reader with excitation wavelength set to 266 nm. A difference between unphosphorylated and phosphorylated ALK-specific biosensors can be observed in FIG. 3A and FIG. 3B, with the phosphorylated ALK-specific biosensor displaying a stronger signal compared to the unphosphorylated artificial peptide-based biosensors.

Figure 4A:
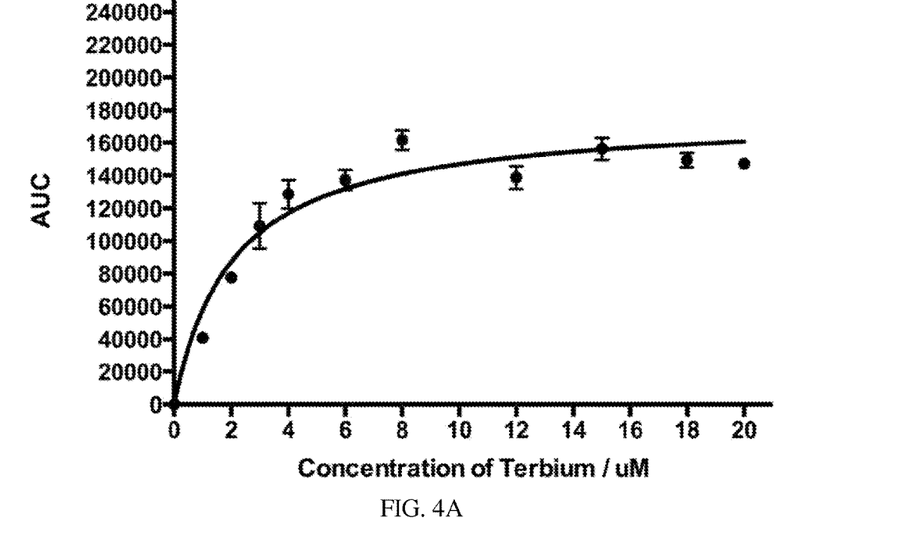
FIG. 4A and FIG. 4B are graphs depicting the binding affinity of terbium to the phosphorylated ALK-specific biosensors, with FIG. 4A depicting the binding affinity of pALAStide-A and FIG. 4B depicting the binding affinity of pALAStide-B.
Figure 4B:
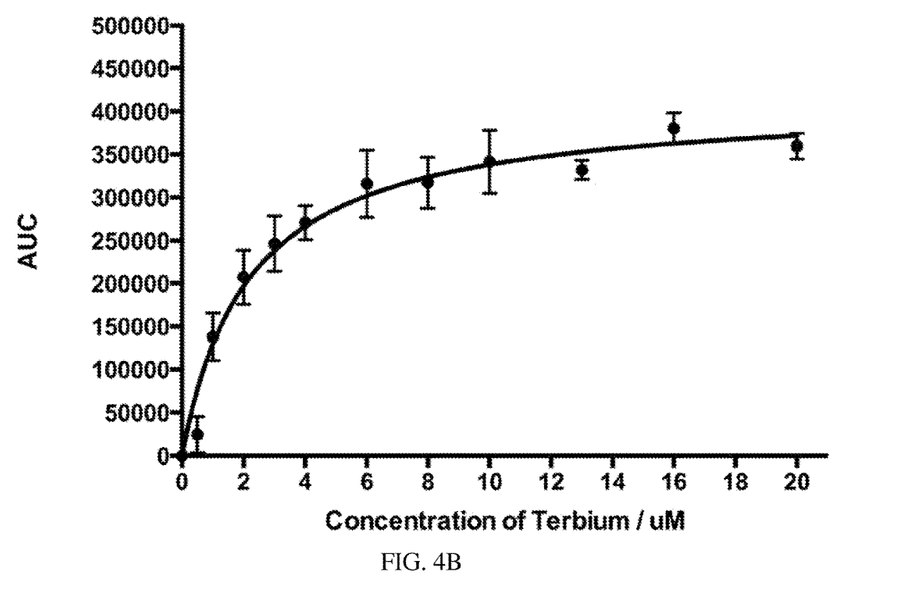

Referring now to FIG. 4A and FIG. 4B, pALAStide-A and pALAStide-B bind $Tb^{3+}$ with high affinity. The dissociation constant ($K_d$) of phosphorylated ALK-specific biosensors and $Tb^{3+}$ are measured by terbium luminescence intensity. The calculated dissociation constant $K_d$ is 2.05±0.30 µM (pALAStide-A) and 2.20±0.28 µM (pALAStide-B). In one example of an experimental approach, 2 µM pALAStide-A or pALAStide-B, various concentrations of $Tb^{3+}$, 100 mM NaCl and 10 mM HEPES buffer (pH=7.5) are used to prepare samples.

Figure 5A:
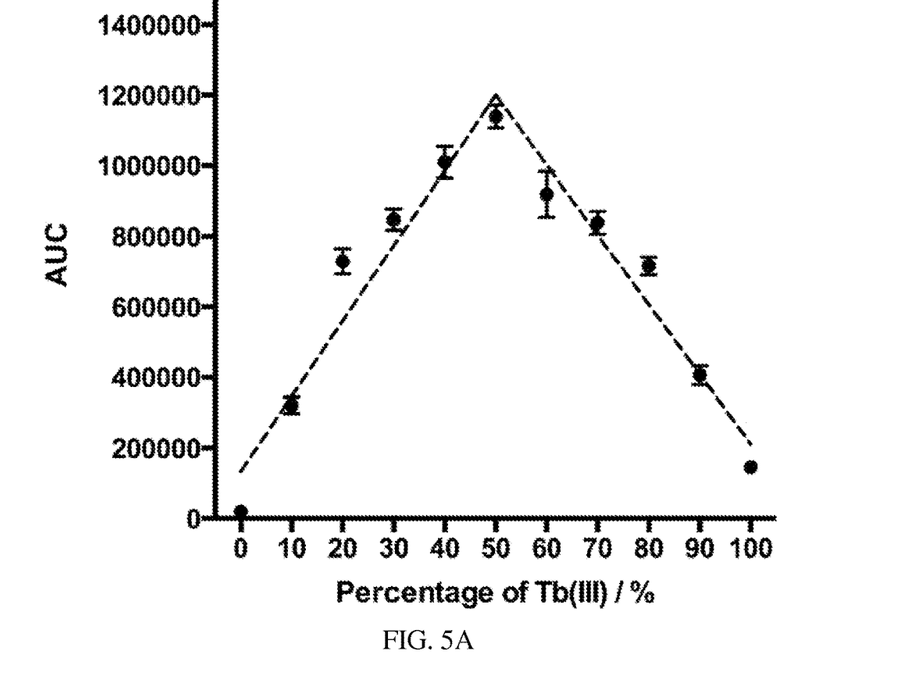
FIG. 5A and FIG. 5B are Job's plots depicting the 1:1 ratio binding of the phosphorylated ALK-specific biosensors with terbium, with FIG. 5A illustrating pALAStide-A and FIG. 5B illustrating pALAStide-B.
Figure 5B:
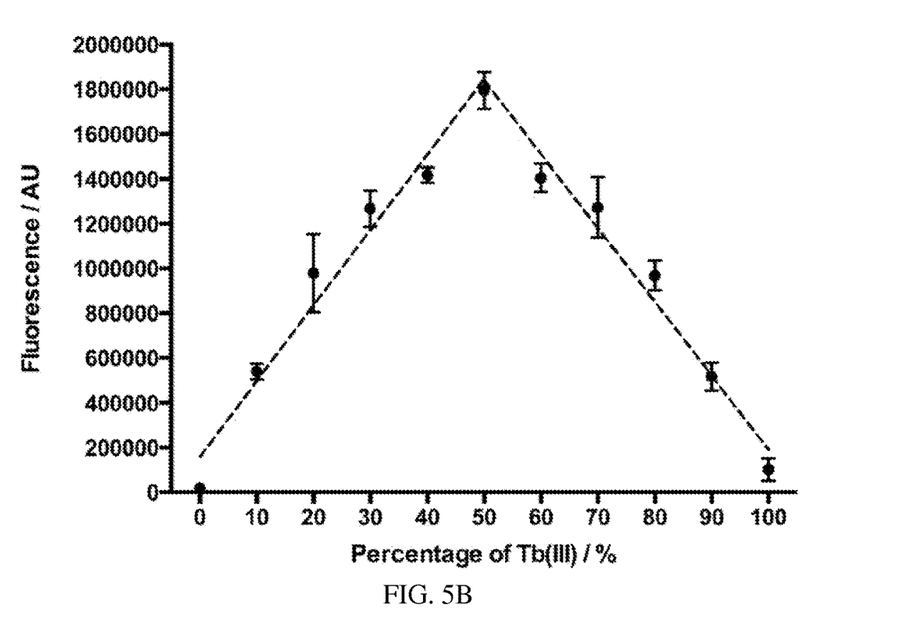

The phosphorylated ALK-specific biosensors binds $Tb^{3+}$ in 1:1 ratio. In an exemplary experiment, the total concentration of pALAStide-A/B and $Tb^{3+}$ was set to 20 µM, while their ratio changes (2 µM pALAStide-A and 18 µM pALAStide-B, 4 µM pALAStide-A and 16 µM pALAStide-B, etc.). The samples also contain 100 mM NaCl and 10 mM HEPES buffer (pH=7.5), and the luminescence signal intensity was measured for each sample. FIGS. 5A and 5B illustrates the 1:1 binding ratio of terbium (III) and the ALK-specific biosensors, pALAStide-A and pALAStide-B, respectively in a Job's plot.

Figure 6A:
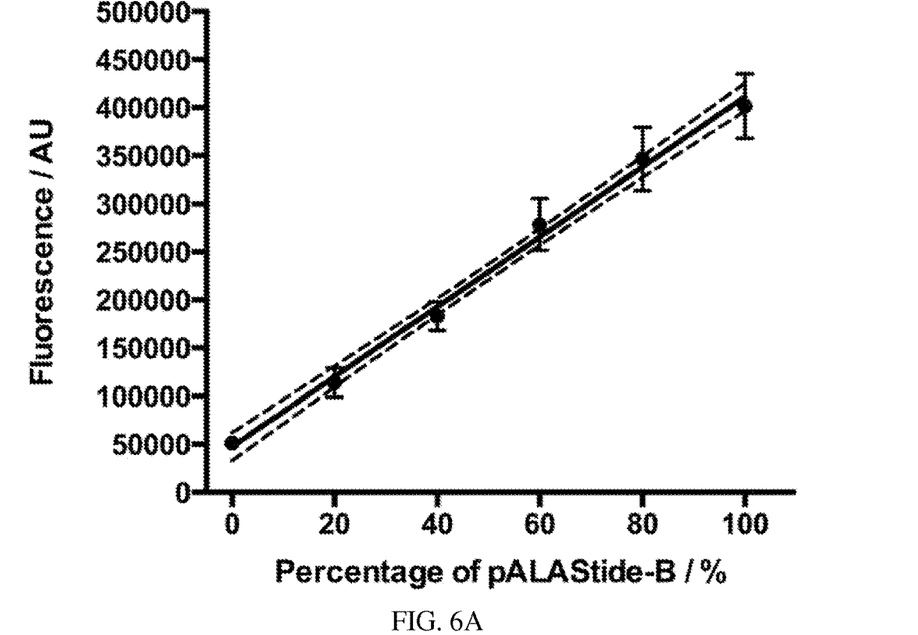
FIG. 6A and FIG. 6B are graphs, with FIG. 6A depicting a standard curve of ALK kinase assay using ALAStide-B, and FIG. 6B depicting a quantitative detection of ALAStide-B phosphorylation.
Figure 6B:
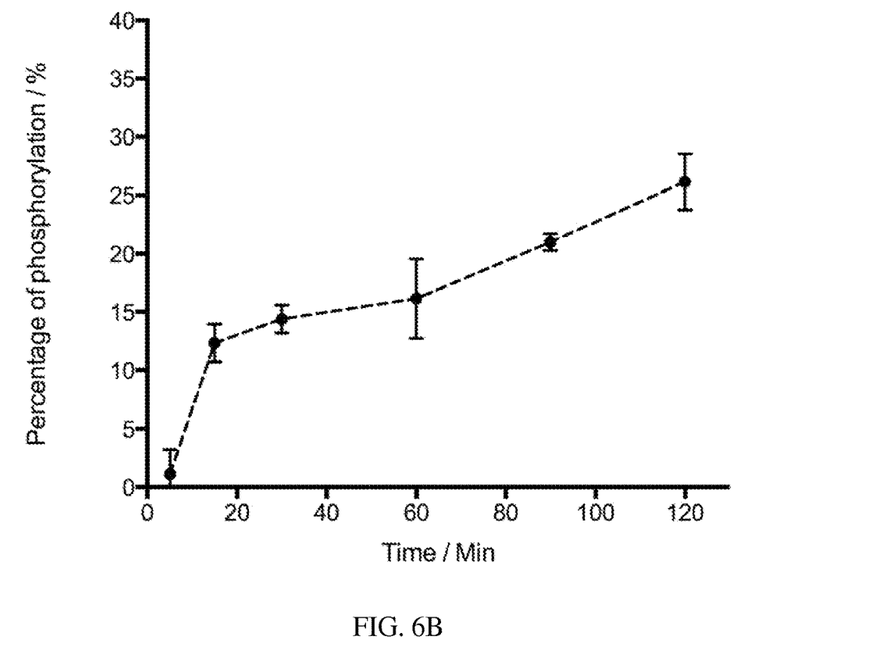

The phosphorylation of ALK-specific biosensors by ALK is quantitatively monitored by $Tb^{3+}$ luminescence. In an exemplary experiment, 25 µM peptides, 0.1 unit kinase, 100 µM ATP, 10 mM $Mg^{2+}$, 25 mM HEPES buffer (pH=7.5) are used. At selected time points, 20 µL sample are taken out and quenched in 20 µL, of 6M urea solution. The quenched sample are later combined with 5 µL of 1 mM $Tb^{3+}$ and 5 µL of 1M NaCl, and then the $Tb^{3+}$ luminescence is measured. A quantitative standard curve can be generated in the same way described above, except replacing the unphosphopeptides with mixture of phosphorylated and unphosphorylated ALK-specific biosensors. The parameters of the assay described in FIG. 6, where FIG. 6A is a standard curve of ALK kinase assay using ALAStide-B and FIG. 6B is the quantitative detection of ALAStide-B phosphorylation, show that the ALK-specific biosensors are capable to be applied in high-throughput screening (HTS) of potential ALK inhibitors (Table 1). To be qualified for HTS application, the Z' factor should be larger than 0.5, and the SW (signal window) should be larger than 2. CV is coefficient of variation. The designed ALK kinase assay using ALK-specific biosensors satisfied these requirements.

Below is a Table 1 showing the high throughput screening (HTS) parameters for the designed assay using $Tb^{3+}$ luminescence with SW standing for signal window, and CV standing for coefficient of variation.

| % Phosphorylation | Z' | SW | CV |
| --- | --- | --- | --- |
| 20% | 0.577 | 5.811 | 0.134 |
| 40% | 0.803 | 17.479 | 0.081 |
| 60% | 0.820 | 16.973 | 0.097 |
| 80% | 0.837 | 18.476 | 0.095 |
| 100% | 0.860 | 21.927 | 0.084 |

The ALK-specific biosensors described have many potential clinical relevant applications. As a reporter of ALK activity, ALK-specific biosensors can be applied in high-throughput screening for potential ALK inhibitors. ALK-specific biosensors can also be conjugated with appropriate delivery modules, such as cell penetrating peptides and affinity tags, so that they can report intracellular ALK activity in living cells and ultimately in biopsies from ALK positive lung cancer patients. In this manner, the ALK-specific biosensors may also serve as diagnostic reagents for ALK positive lung cancer patients, and other diseases that are associated with a misregulated or an aberrant ALK enzyme.

Figure 7:
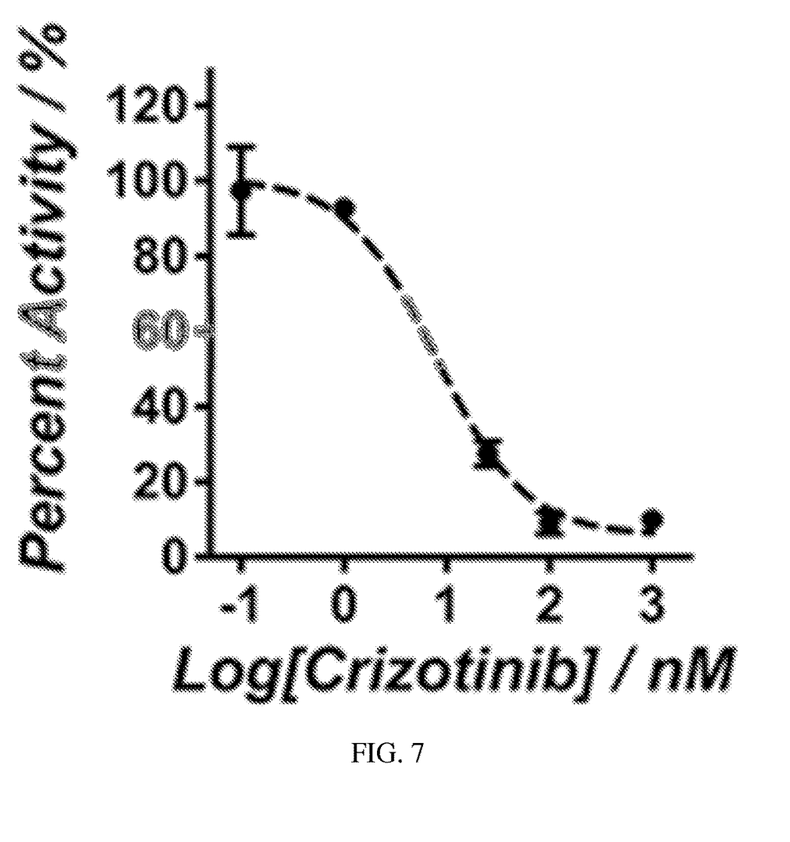
FIG. 7 is a graph showing dose-response inhibition of ALK by crizotinib as measured by ALAStide-A.

Referring now to FIG. 7, the ALK-specific biosensors were tested in an ALK inhibition assay using a known ALK inhibitor, crizotinib. In one exemplary assay, recombinant active ALK kinase domain was incubated at 37° C. with the kinase reaction buffer described above, including dimethylsulfoxide (DMSO, Sigma, USA) or various concentrations of crizotinib (Selleck Chemicals, USA), for 5 min prior to the start of the reaction. The final concentration of DMSO was limited to 0.1% v/v in each sample. The kinase reactions were initiated by adding ALK-specific biosensors to a final concentration of 100 µM (in a total volume of 20 µL). Each reaction was quenched after 90 min in 20 µL 6 M urea, followed by addition of the luminescence buffer and luminescence measurement as described above.

The contents of U.S. patent application Ser. No. 13/761,968 filed Feb. 7, 2013 and U.S. Provisional Application Nos. 61/595,959 filed Feb. 7, 2012, 61/603,752 filed Feb. 27, 2012, 61/605,591 filed Mar. 1, 2012, 61/693,002 filed Aug. 24, 2012, 61/704,298 filed Sep. 21, 2012, and 61/736,312 filed Dec. 12, 2012, are each incorporated by reference in its entirety.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected

The invention claimed is:

1. An ALK-specific biosensor comprising:
a peptide comprising a substrate sequence, the substrate sequence comprising a core sequence $FX_2MX_4RDX_7YX_9X_{10}X_{11}FFRRKGG$ (SEQ ID NO:12), wherein
$X_2$ is G or D;
$X_4$ is A or D;
$X_7$ is I or H;
$X_9$ is R or T;
$X_{10}$ is M, D, or N; and
$X_{11}$ is S or T.

2. The ALK-specific biosensor of claim 1, further including a cell penetrating peptide coupled to the ALK-specific biosensor.

3. The ALK-specific biosensor of claim 1, further including an affinity tag coupled to the ALK-specific biosensor.

4. The ALK-specific biosensor of claim 1, wherein the biosensor binds terbium when phosphorylated.

5. The ALK-specific biosensor of claim 1, wherein the biosensor comprises the sequence (SEQ ID NO: 1) FDMDRDIYRMSFFRKGGK$_b$GG, and wherein K$_b$ is biotinylated lysine.

6. An ALK-specific biosensor comprising:
a peptide comprising a substrate sequence, the substrate sequence comprising a core sequence $FX_2MX_4RDX_7YX_9X_{10}X_{11}FFRRKGG$ (SEQ ID NO:11), wherein $X_2$ is a polar uncharged amino acid or polar acidic amino acid;

$X_4$ is a nonpolar hydrophobic amino acid, polar uncharged amino acid, or polar acidic amino acid;

$X_7$ is a nonpolar hydrophobic amino acid or polar basic amino acid;

$X_9$ is a polar basic amino acid or polar uncharged amino acid;

$X_{10}$ is a nonpolar hydrophobic amino acid, a polar acidic amino acid, or a polar uncharged amino acid; and $X_{11}$ is a polar uncharged amino acid.

7. The ALK-specific biosensor of claim 6, further including a cell penetrating peptide coupled to the ALK-specific biosensor.

8. The ALK-specific biosensor of claim 6, further including an affinity tag couple to the ALK-specific biosensor.

9. The ALK-specific biosensor of claim 6, wherein the biosensor binds terbium when phosphorylated.

10. The ALK-specific biosensor of claim 6, wherein the biosensor comprises the sequence (SEQ ID NO: 1) FDMDRDIYRMSFFRKGGK$_b$GG, and wherein K$_b$ is biotinylated lysine.

* * * * *

SEQUENCE LISTING

<160> NUMBER OF SEQ ID NOS: 12

<210> SEQ ID NO 1
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (18)..(18)
<223> OTHER INFORMATION: Biotinylated Lysine

<400> SEQUENCE: 1

Phe Asp Met Asp Arg Asp Ile Tyr Arg Met Ser Phe Phe Arg Lys Gly
1               5                   10                  15

Gly Lys Gly Gly
            20

<210> SEQ ID NO 2
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (18)..(18)
<223> OTHER INFORMATION: Biotinylated Lysine

<400> SEQUENCE: 2

Phe Asp Met Asp Arg Asp Ile Tyr Thr Asn Thr Phe Phe Arg Lys Gly
1               5                   10                  15

Gly Lys Gly Gly
            20

<210> SEQ ID NO 3
<211> LENGTH: 20
<212> TYPE: PRT
<213> ORGANISM: Artificial Sequence
<220> FEATURE:
<223> OTHER INFORMATION: Synthesized

<400> SEQUENCE: 3

Phe Asp Met Asp Arg Asp Ile Tyr Arg Met Ser Phe Phe Arg Lys Gly
1               5                   10                  15

Gly Lys Gly Gly
            20

<210> SEQ ID NO 4
<211> LENGTH: 20
<212> TYPE: PRT
<213> ORGANISM: Artificial Sequence
<220> FEATURE:
<223> OTHER INFORMATION: Synthesized

<400> SEQUENCE: 4

Phe Asp Met Asp Arg Asp Ile Tyr Thr Asn Thr Phe Phe Arg Lys Gly
1               5                   10                  15

Gly Lys Gly Gly
            20

<210> SEQ ID NO 5
<211> LENGTH: 20
<212> TYPE: PRT
<213> ORGANISM: Artificial Sequence

```
<220> FEATURE:
<223> OTHER INFORMATION: Synthesized
<220> FEATURE:
<221> NAME/KEY: MOD_RES
<222> LOCATION: (18)..(18)
<223> OTHER INFORMATION: Biotinylated Lysine

<400> SEQUENCE: 5

Phe Asp Met Asp Arg Asp Ile Tyr Arg Asp Ser Phe Phe Arg Lys Gly
1               5                   10                  15

Gly Lys Gly Gly
            20

<210> SEQ ID NO 6
<211> LENGTH: 20
<212> TYPE: PRT
<213> ORGANISM: Artificial Sequence
<220> FEATURE:
<223> OTHER INFORMATION: Synthesized

<400> SEQUENCE: 6

Phe Asp Met Asp Arg Asp Ile Tyr Arg Asp Ser Phe Phe Arg Lys Gly
1               5                   10                  15

Gly Lys Gly Gly
            20

<210> SEQ ID NO 7
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (18)..(18)
<223> OTHER INFORMATION: Biotinylated Lysine

<400> SEQUENCE: 7

Phe Asp Met Asp Arg Asp Ile Tyr Arg Asn Thr Phe Phe Arg Lys Gly
1               5                   10                  15

Gly Lys Gly Gly
            20

<210> SEQ ID NO 8
<211> LENGTH: 20
<212> TYPE: PRT
<213> ORGANISM: Artificial Sequence
<220> FEATURE:
<223> OTHER INFORMATION: Synthesized

<400> SEQUENCE: 8

Phe Asp Met Asp Arg Asp Ile Tyr Arg Asn Thr Phe Phe Arg Lys Gly
1               5                   10                  15

Gly Lys Gly Gly
            20

<210> SEQ ID NO 9
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (18)..(18)
<223> OTHER INFORMATION: Biotinylated Lysine
```

-continued

<400> SEQUENCE: 9

Phe Gly Met Ala Arg Asp Ile Tyr Arg Ala Ser Phe Phe Arg Lys Gly
1               5                   10                  15

Gly Lys Gly Gly
            20

<210> SEQ ID NO 10
<211> LENGTH: 9
<212> TYPE: PRT
<213> ORGANISM: Artificial Sequence
<220> FEATURE:
<223> OTHER INFORMATION: Synthesized

<400> SEQUENCE: 10

Arg Lys Lys Arg Arg Gln Arg Arg Arg
1               5

<210> SEQ ID NO 11
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (2)..(2)
<223> OTHER INFORMATION: X2 is a polar uncharged amino acid or polar
      acidic amino acid
<220> FEATURE:
<221> NAME/KEY: VARIANT
<222> LOCATION: (4)..(4)
<223> OTHER INFORMATION: X4 is a nonpolar hydrophobic amino acid, polar
      uncharged amino acid, or polar acidic amino acid
<220> FEATURE:
<221> NAME/KEY: VARIANT
<222> LOCATION: (7)..(7)
<223> OTHER INFORMATION: X7 is a nonpolar hydrophobic amino acid or
       polar basic amino acid
<220> FEATURE:
<221> NAME/KEY: VARIANT
<222> LOCATION: (9)..(9)
<223> OTHER INFORMATION: X9 is a polar basic amino acid or polar
      uncharged amino acid
<220> FEATURE:
<221> NAME/KEY: VARIANT
<222> LOCATION: (10)..(10)
<223> OTHER INFORMATION: X10 is a nonpolar hydrophobic amino acid, a
      polar acidic amino acid, or a polar uncharged amino acid
<220> FEATURE:
<221> NAME/KEY: VARIANT
<222> LOCATION: (11)..(11)
<223> OTHER INFORMATION: X11 is a polar uncharged amino acid

<400> SEQUENCE: 11

Phe Xaa Met Xaa Arg Asp Xaa Tyr Xaa Xaa Xaa Phe Phe Arg Arg Lys
1               5                   10                  15

Gly Gly

<210> SEQ ID NO 12
<211> LENGTH: 17
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (2)..(2)
<223> OTHER INFORMATION: X2 is G or D

```
<220> FEATURE:
<221> NAME/KEY: VARIANT
<222> LOCATION: (4)..(4)
<223> OTHER INFORMATION: X4 is A or D
<220> FEATURE:
<221> NAME/KEY: VARIANT
<222> LOCATION: (7)..(7)
<223> OTHER INFORMATION: X7 is I or H
<220> FEATURE:
<221> NAME/KEY: VARIANT
<222> LOCATION: (9)..(9)
<223> OTHER INFORMATION: X9 is R or T
<220> FEATURE:
<221> NAME/KEY: VARIANT
<222> LOCATION: (10)..(10)
<223> OTHER INFORMATION: X10 is M, D, or N
<220> FEATURE:
<221> NAME/KEY: VARIANT
<222> LOCATION: (11)..(11)
<223> OTHER INFORMATION: X11 is S, or T

<400> SEQUENCE: 12

Phe Xaa Met Xaa Arg Asp Xaa Tyr Xaa Xaa Xaa Phe Phe Arg Lys Gly
1               5                   10                  15

Gly
```